United States Patent
Chierchia et al.

(10) Patent No.: US 11,359,243 B2
(45) Date of Patent: Jun. 14, 2022

(54) METHOD FOR THE DIAGNOSIS AND PROGNOSIS OF NEURODEGENERATIVE AND NEUROINFLAMMATORY PATHOLOGIES

(71) Applicant: BRAINDTECH S.P.A., Milan (IT)

(72) Inventors: Armando Chierchia, Milan (IT); Fabio Bianco, Milan (IT)

(73) Assignee: BRAINDTECH S.P.A., Milan (IT)

( * ) Notice: Subject to any disclaimer, the term of this patent is extended or adjusted under 35 U.S.C. 154(b) by 0 days.

(21) Appl. No.: 16/649,247

(22) PCT Filed: Sep. 20, 2018

(86) PCT No.: PCT/IB2018/057261
§ 371 (c)(1),
(2) Date: Mar. 20, 2020

(87) PCT Pub. No.: WO2019/058303
PCT Pub. Date: Mar. 28, 2019

(65) Prior Publication Data
US 2020/0216902 A1 Jul. 9, 2020

(30) Foreign Application Priority Data
Sep. 21, 2017 (IT) .................. 102017000105483

(51) Int. Cl.
*C12Q 1/6883* (2018.01)
*G01N 1/28* (2006.01)
*G01N 33/543* (2006.01)

(52) U.S. Cl.
CPC ............ *C12Q 1/6883* (2013.01); *G01N 1/28* (2013.01); *G01N 33/543* (2013.01); *C12Q 2600/178* (2013.01); *G01N 2800/2814* (2013.01); *G01N 2800/2821* (2013.01); *G01N 2800/52* (2013.01)

(58) Field of Classification Search
CPC .. C12Q 1/6883; C12Q 2600/178; G01N 1/28; G01N 33/543; G01N 2800/2814; G01N 2800/2821; G01N 2800/52; G01N 2800/28; G01N 33/6896
See application file for complete search history.

(56) References Cited

FOREIGN PATENT DOCUMENTS

WO       2015061634        4/2015

OTHER PUBLICATIONS

Bianco et al. (2009) Acid sphingomyelinase activity triggers microparticle release from glial cells. EMBO J. 28, 1043-54 (Year: 2009).*
Crescitelli et al. (2013) Distinct RNA profiles in subpopulations of extracellular vesicles: apoptotic bodies, microvesicles and exosomes. J. Extracell. Vesicles 2, 20677 (Year: 2013).*
MinElute Handbook published Mar. 2006 (Year: 2006).*
Chen et al., (2010). Microfluidic isolation and transcriptome analysis of serum microvesicles. Lab Chip 10: 505-511 (Year: 2010).*
Agosta F et al., "Myeloid microvesicles in cerebrospinal fluid are associated with myelin damage and neuronal loss in mild cognitive impairment and Alzheimer disease", American Neurological Association, pp. 813-825, vol. 76, No. 6 (2014).
Bennett ML et al., "New tools for studying microglia in the mouse and human CNS", Proc Natl Acad Sci, pp. E1738-E1746, vol. 113, No. 12, (Feb. 2016).
Bohlen et al., "Diverse Requirements for Microglial Survival, Specification, and Function Revealed by Defined-Medium Cultures", Neuron, Cell Press, pp. 759-773, vol. 94 (May 2017).
Satoh et al., "TMEM119 marks a subset of microglia in the human brain" Neuropathology, pp. 39-49, vol. 36, No. 1, (Feb. 2016).
Thompson et al., "Extracellualr vesicles in neurodegenerative disaease-pathogenesis to biomarkers" Nature Reviews Neurology, pp. 346-357, vol. 12, (May 2016).
Nigro et al.," Myeloid extracellular vesicles: Messengers from the Demented Brain", Frontiers in Immunology, pp. 1-5, vol. 7 (Jan. 2016).
Sadallah et al., Microparticles (Ectosomes) Shed by Stored Human Platelets Downregulate Macrophages and Modify the Development of Dendritic Cells, J Immunol., 186:6543-6552 (2011).
Turola et al., Microglial microvesicle secretion and intercellular signaling, Frontiers in Physiology, vol. 3, Article 149, pp. 1-11 (2012).
Simons et al., Exosomes—vesicular carriers for intercellular communication, Current Opinions in Cell Biology, 21:575-581 (2009).
Cocucci et al., Shedding microvesicles: artefacts no more, Trends in Cell Biology, 19(2):43-51 (2009).

* cited by examiner

*Primary Examiner* — Kimberly Ballard
*Assistant Examiner* — Stacey N Macfarlane
(74) *Attorney, Agent, or Firm* — Browdy and Neimark, PLLC

(57) ABSTRACT

The present invention relates to a method for the early diagnosis and prognosis of an inflammatory state of the brain, caused by neurological, neurodegenerative, and/or aging diseases. Said method is based on the qualitative-quantitative evaluation of microglia microvesicles in a subject's plasma.

2 Claims, 4 Drawing Sheets
Specification includes a Sequence Listing.

METHOD FOR THE DIAGNOSIS AND PROGNOSIS OF NEURODEGENERATIVE AND NEUROINFLAMMATORY PATHOLOGIES

The present invention relates to a method for the early diagnosis and prognosis of an inflammatory state of the brain, caused by neurological, neurodegenerative, and/or aging diseases. Said method is based on the qualitative-quantitative evaluation of microglia microvesicles in a subject's plasma.

PRIOR ART

The identification and validation of biomarkers for the diagnosis and prognosis of Alzheimer's disease (AD) and of other forms of dementia and diseases related to neuroinflammation and/or neurodegeneration and aging such as, for example, Parkinson's disease, multiple sclerosis, neuropathic pain, are increasingly important.

To date, quantitative measurement through the ELISA assay of β-amyloid (1-42), total tau and phospho-tau-181 in the cerebrospinal fluid (CSF) is the most advanced and accepted method to diagnose the probability of onset of AD.

In the CSF, an increase in microglia microvesicles correlated with neuroinflammation and with AD has been demonstrated (Agosta F et al., Myeloid microvesicles in cerebrospinal fluid are associated with myelin damage and neuronal loss in mild cognitive impairment and Alzheimer disease. Ann Neurol. 2014 76(6):813-25).

A marker which can selectively identify microglia, discriminating it from other cells in the myeloid system, has recently been identified. Said marker is the transmembrane protein 119 (Tmem119) (Bennett ML et al., New tools for studying microglia in the mouse and human CNS. Proc Natl Acad Sci USA 2016 113(12):E1738-46). Bennett et al. describe monoclonal antibodies capable of recognizing the intracellular and extracellular domains of Tmem119, allowing an immunological staining of the microglia in histological sections of the brain.

The identification of new biomarkers, the measurement of which is reproducible and preferably possible in blood samples, remains a major challenge.

DESCRIPTION OF THE INVENTION

The authors of the present invention have surprisingly shown that microglia microvesicles are present in the blood samples of patients affected by neuroinflammatory, neurodegenerative and/or aging diseases, such as AD and Frontotemporal Dementia (FTD), but not in healthy individuals.

Therefore, the present invention relates to a method for the early diagnosis of an inflammatory state of the brain, caused by neurological, neurodegenerative, inflammatory, and/or aging diseases, where said method comprises the quantitative-quantitative measurement of microglia microvesicles in plasma samples.

Said method comprises:
Fractionation of a plasma sample with isolation of the microvesicle fraction, where said fractionation occurs by centrifuging said plasma sample at about 14,000 g for a time of between 10 seconds and 40 minutes, preferably for about 30 minutes, or for 20 minutes;
Analysis of said micro-vesicle fraction for the identification of microglia microvesicles; where the presence in said sample of said microglia microvesicles is indicative of a neuroinflammatory, neurodegenerative and/or neurological and/or aging disease.

Said microglia microvesicle identification is carried out by methods known to those skilled in the art. In a preferred embodiment, said method comprises the measurement in the microglia microvesicle fraction isolated from said plasma sample of one or more specific microglia microvesicle markers. In a preferred embodiment, said at least one marker is Tmem119.

The advantage associated with Tmem119 is related to the fact that a prolonged stability of the same in the plasma has been surprisingly observed herein.

In one embodiment, said one or more markers are measured by immunological methods. In a further embodiment, the measurement is performed by molecular analysis.

The method according to the present invention has been surprisingly advantageous in the early diagnosis of neurodegenerative diseases and neurological diseases.

In one embodiment, the analysis of said microglia microvesicles is a quantitative analysis, where the concentration of said microglia microvesicles in plasma is correlated with the degree of severity of the neuroinflammatory, neurodegenerative and/or neurological disease.

Figure 1:
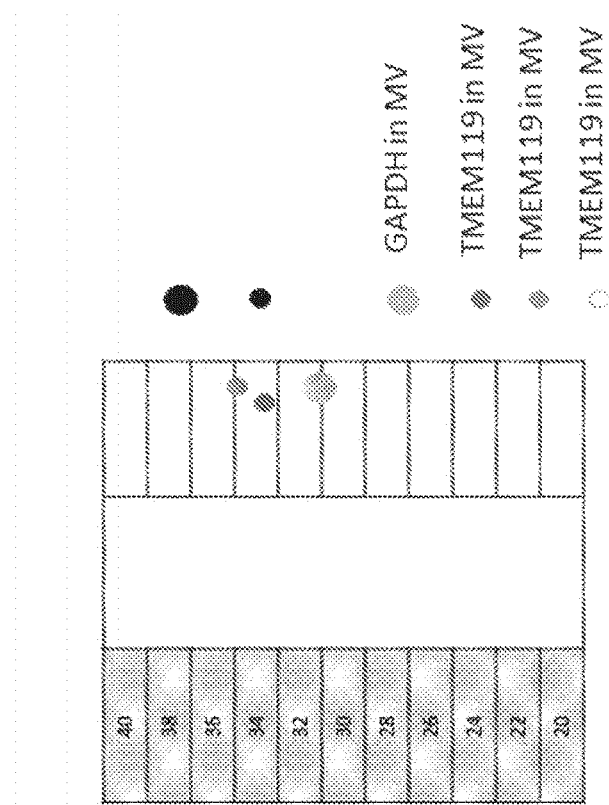
FIG. 1: Tmem119 molecular analysis on blood control samples and blood samples from patients with AD or FTD.

Molecular and immunological assays carried out on plasma samples of control subjects and subjects suffering from neuroinflammatory and/or neurodegenerative diseases from which the microvesicles were isolated by methods known to those skilled in the art show that the microvesicular population present in the plasma comprises microglia microvesicles only in samples affected by neuroinflammatory and/or neurodegenerative diseases. Surprisingly, the authors of the present invention have shown that microglia microvesicles are not present in the plasma of control subjects, where said control subjects are age-homogeneous subjects compared to the analyzed pathological subjects, all the subjects being aged between 72 and 80 years.

Microglia microvesicles also increase in plasma as the disease progresses, making the measurement thereof an elective method for monitoring said diseases.

The availability of Tmem119 as a specific and stable microglia microvesicle marker makes the diagnostic and prognosis method according to the present invention an elective method for the diagnosis and/or prognosis of neuroinflammatory and/or neurodegenerative and/or neurological diseases.

In a preferred embodiment, the microglia microvesicles are isolated by centrifuging a plasma sample at about 14,000 g for a time ranging from 10 seconds to 40 minutes, preferably 20 minutes, or 2 minutes.

Alternatively, said microvesicles are isolated by FACS sorting, or by immunoaffinity assay with beads, or by exclusion chromatography.

Example 1: Identification by Molecular Analysis of Tmem119 in Plasma Samples

500 µl of plasma were collected from subjects classified as control subjects, subjects suffering from AD, subjects suffering from FTD. Subjects were selected from homogeneous ages between 72 and 80 years. The microvesicles were isolated by methods known to those skilled in the art. Specifically, the microvesicles were isolated as follows:

1. Centrifugation of the plasma at 300 g for 5 minutes at +4° C.;
2. Transfer of the supernatant into a new 1.5 ml tube;
3. Centrifugation of the supernatant at 14000 g for 30 minutes at +4° C., with consequent precipitation of the microvesicles;
4. Transfer of the supernatant into a new 1.5 ml tube;
5. Total RNA extraction from the pellet obtained by the centrifugation referred to in step 4.

Total RNA was extracted using the miRCURY RNA isolation kit (CELL & PLANT #588711, Exiqon), using the following procedure: 350 µl of lysis buffer, comprising β-mercaptoethanol 10 µl/ml, were added to the precipitate which was then vortexed for 10 sec. 200 µl of pure ethanol were added to the resulting lysate and vortexed for 10 sec. The lysate was loaded onto a column which then centrifuged at 3500 g for 1 min. The eluate was eliminated and the column reassembled, repeating the centrifugation step until the lysate was completely eluted.

For DNA removal, 35 µl of DNA Digestion Buffer and 5 µL of DNase I (Zymo Research DNase I # ZYE1010) were mixed and added directly to the column matrix and incubated for 15 min at room temperature. 400 µl of wash solution were then applied and centrifuged at 14000 g for 1 min. After removal of the eluate, the column was reassembled and 400 µl of wash solution were applied and centrifuged at 14000 g for 1 min. The operation was repeated by centrifuging at 14000 g for 2 min so as to thoroughly dry the resin. The eluate was removed and the column placed in a new 1.7 ml elution tube. Then, 5 µl of elution buffer were added and the column was centrifuged at 200 g for 2 min and then at 14000 g for 1 min.

The total RNA concentration was evaluated with a Nanodrop ND-1000 spectrophotometer.

The purity, A260/280 ratio and A260/230 ratio, and the concentration of the isolated RNA were measured using a NanoDrop ND-1000 spectrophotometer.

100 ng of total RNA extract were retrotranscribed with Superscript IV VILO Master MIX with ezDNase (#11766050, Invitrogen), according to the manufacturer's protocol. qRT-PCR was performed with 20 ng cDNA, with TaqMan Gene Expression Master Mix (#1611275, Applied Biosystems, Thermo Fisher Scientific) and the TaqMan gene expression assay for TMEM119 (Hs01938722_u, 174 bp Thermo Fisher Scientific) and GAPDH (Hs02758991_g1, 93 bp; Thermo Fisher Scientific). All samples were tested in duplicate on a real-time ABI PRISM 7500 PCR system.

The results, shown in FIG. 1, clearly show the expression of TMEM119 in the samples obtained from AD subjects and from FTD subjects. No signal was detected in the control subjects.

Example 2: Tmem119 Analysis with Immunofluorescence

500 µl of plasma were collected from subjects classified as control subjects and subjects suffering from AD. The pellet containing the microvesicles was obtained as described in example 1. The pellet was resuspended in the Krebs Ringer solution, which was then loaded into a microchannel where the vesicles were free to flow up to reach the beads coated with Annexin V. The microvesicles expose phosphatidylserine to the outer sheet of the plasma membrane and bind Annexin V, thus being captured by the Annexin V beads. The beads were then fixated in 4% paraformaldehyde for 10-15 min, then washed with buffered phosphate saline containing 0.1% Triton-X-100 (PBST).

Subsequently, the microvesicles were labeled with the TMEM119 antibody (sc244341, Santa Cruz), shown with a secondary fluorescent antibody (Molecular Probes). The images were acquired using an inverted Motic AE31E microscope.

Figure 2:
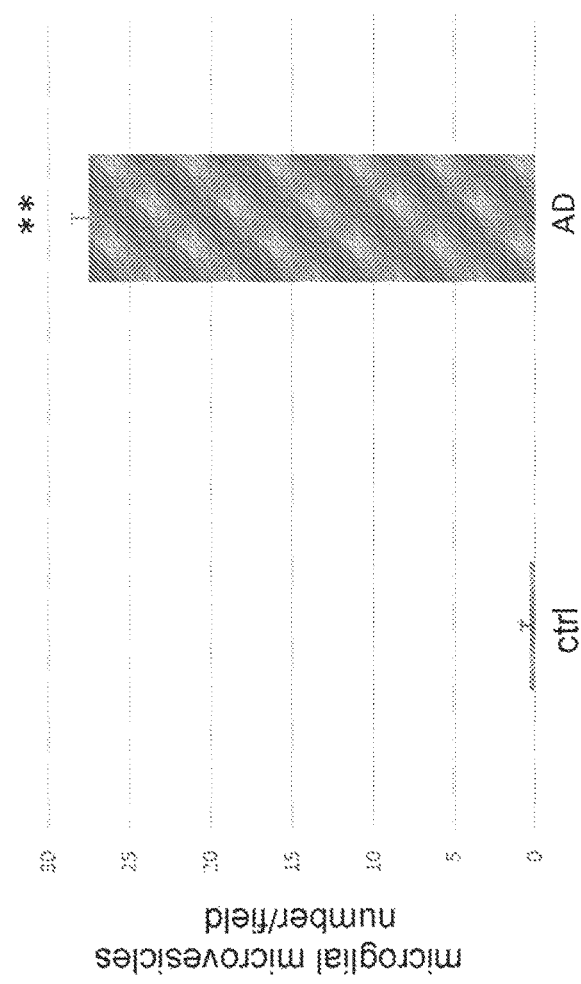
FIG. 2: immunological analysis of Tmem119 on blood control samples and blood samples from patients with AD.

The data shown in the graph in FIG. 2 are indicative of the counts carried out in 6 fields for each of the samples tested. As can be seen from the graph, the staining with Tmem119 is present in the AD samples but not in the control samples.

Example 3: Sample Processing for Microglia Microvesicle Isolation

The plasma was collected from 7 subjects affected by AD, then divided into two aliquots.

A first aliquot, of 500 µl, was processed according to the protocol detailed in example 1 for the isolation of microvesicles.

A second aliquot, of 500 µl, was processed according to the protocol described in WO2015/061634. In short, 100 µl of thromboplastin D (Fisher Scientific, Inc., Hanover Park, Ill.) were added to the 500 µl of plasma and the sample was incubated at room temperature for 30'. The sample was then subjected to a centrifugation at 1,500 g for 5 minutes and the supernatant was collected. After mixing the same with the exosome precipitation solution (ExoQuick, System Biosciences, Inc., Mountainview, Calif.) and incubating for 1 h to 4° C., the suspension underwent a further centrifugation at 1500 g for 30'. The pellet thus obtained was used for the following analysis.

Figure 3:
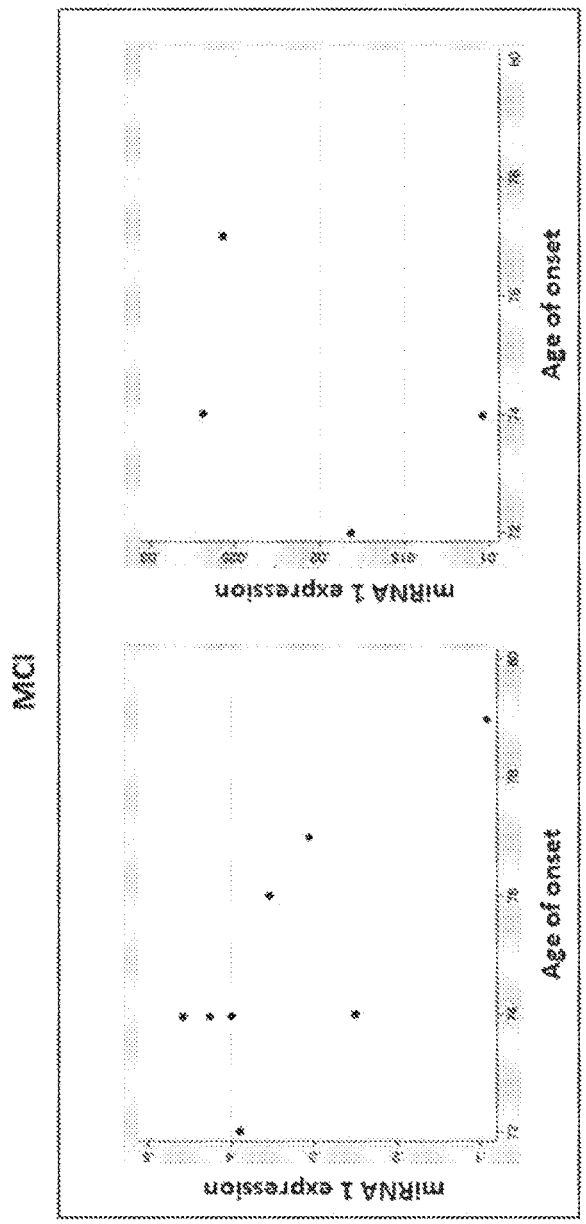
FIG. 3: miRNA 1 expression in samples processed according to the method of the invention (A) or with a comparative method (B).

The samples, obtained with the protocol according to the invention or with the comparative protocol, were then tested for the presence of a specific miRNA, in this example the quantitative evaluation of the miRNA hsa-miR-4662a-5p (miRNA1) is reported. The data obtained are shown in FIG. 3 and show the correlation of miRNA1 expression levels with respect to the age of onset of the disease in 7 plasma samples examined from the 7 AD patients. In the graph on the left, which shows the data relating to the analysis of microglia microvesicle content obtained by the protocol according to the invention, it is possible to appreciate an indirect correlation between miRNA 1 expression levels and the age of onset of the disease, with the levels of expression which decrease as the age of onset of the disease increases. In the graph on the right, which shows the data related to the analysis following the protocol described in WO2015/061634, no correlation is observed. Furthermore, only data from 4 patients are present because not all samples isolated by the procedure of WO2015/061634 showed an expression of miRNA1. This indicates that the procedure according to the present invention, but not the method according to the prior art cited, surprisingly succeeds in isolating the fraction of interest from the plasma.

Example 4: Identification and Count of Microglia Microvesicles by FACS

Preparation and calibration of the instrument (CitoFlex Beckman Culter) for the identification and counting of microglia microvesicles was performed following the procedures of the instrument manual; in particular, a mix of fluorescent beads for FACS with different sizes, 100, 160, 200, 240, 300, 500, 900nm (the "Gigamix solution" mix) was prepared.

After having appropriately vortexed the Gigamix beads, their passage was recorded so as to be able to create a calibration curve with respect to the size of the microvesicles of interest, setting the Gain and Threshold parameters.

The sample containing the microglia microvesicles isolated according to the procedure of example 1 was stained with a cytoplasmic dye (CSFE 2 uM) and subsequently quantified by FACS analysis.

Figure 4:
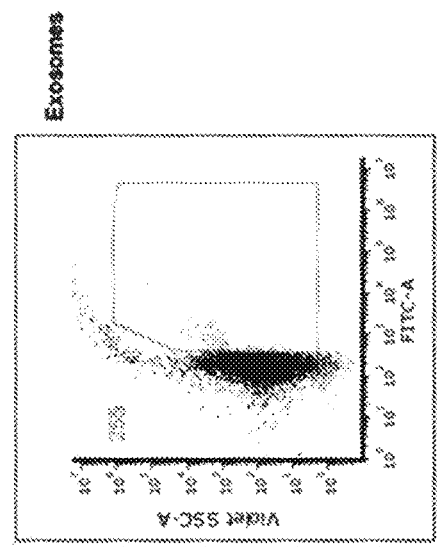
FIG. 4: representative image of microglia microvesicle isolation by FACS.

The graphs shown in FIG. 4 show the calibration with beads (left graph), and the sample containing microglia microvesicles (central graph) but not exosomes (right graph), demonstrating the ability to discriminate and collect the microvesicle sample with respect to the exosomes.

Example 5: Development of TEM119-Specific Antibody, Extracellular Portion

Figure 5:
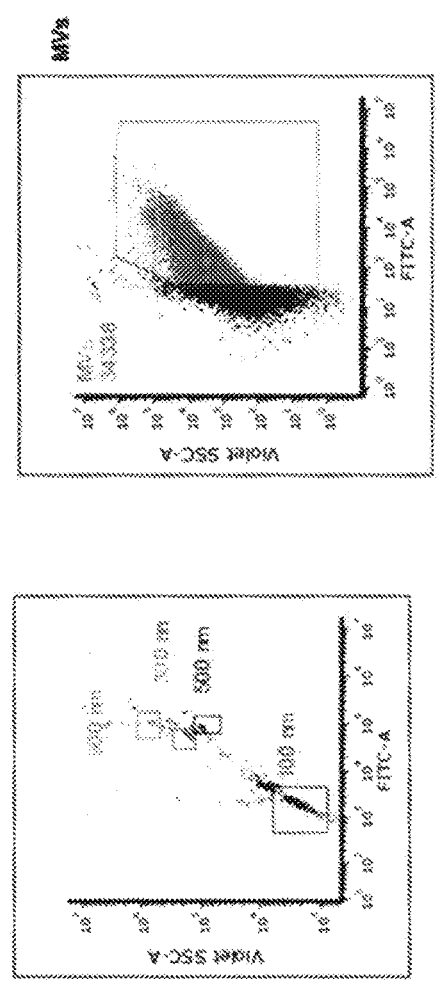
FIG. 5: TMEM119 amino acid sequence. The extracellular portion 29-96 is highlighted in gray.

The TMEM119 protein is a transmembrane protein. The amino acid sequence (SEQ ID No. 1) is shown in FIG. 5. For the isolation of the antibody, two sequences capable of recognizing the extracellular portion of TMEM119 were used. The first sequence (SEQ ID no. 2) is VAGSGEAEGSSASS, the second sequence (SEQ ID no. 3) is MGPQPITLGGPSPPTN.

The invention claimed is:

1. A method for detecting the presence of microglia microvesicles to identify a subject with Alzheimer's disease (AD) and/or Frontotemporal Dementia (FTD), comprising:
   centrifuging a plasma sample from a subject at about 14,000 g for a period of time between 10 seconds and 40 minutes to precipitate the microvesicle fraction;
   isolating said microvesicle fraction;
   contacting microvesicles in said isolated microvesicle fraction with an anti-TMEM119 antibody; and
   detecting an increase in the amount of microglia microvesicles isolated from the plasma with the anti-TMEM119 antibody to identify the subject as having Alzheimer's disease (AD) and/or Frontotemporal Dementia (FTD).

2. The method according to claim 1, wherein the anti-TMEM119 antibody is anti-TMEM119 antibody sc244341.

* * * * *

SEQUENCE LISTING

```
<160> NUMBER OF SEQ ID NOS: 3

<210> SEQ ID NO 1
<211> LENGTH: 283
<212> TYPE: PRT
<213> ORGANISM: Homo sapiens

<400> SEQUENCE: 1

Met Val Ser Ala Ala Ala Pro Ser Leu Leu Ile Leu Leu Leu Leu
1               5                   10                  15

Leu Gly Ser Val Pro Ala Thr Asp Ala Arg Ser Val Pro Leu Lys Ala
                20                  25                  30

Thr Phe Leu Glu Asp Val Ala Gly Ser Gly Glu Ala Glu Gly Ser Ser
            35                  40                  45

Ala Ser Ser Pro Ser Leu Pro Pro Pro Trp Thr Pro Ala Leu Ser Pro
        50                  55                  60

Thr Ser Met Gly Pro Gln Pro Ile Thr Leu Gly Gly Pro Ser Pro Pro
65                  70                  75                  80

Thr Asn Phe Leu Asp Gly Ile Val Asp Phe Phe Arg Gln Tyr Val Met
                85                  90                  95

Leu Ile Ala Val Val Gly Ser Leu Ala Phe Leu Leu Met Phe Ile Val
                100                 105                 110

Cys Ala Ala Val Ile Thr Arg Gln Lys Gln Lys Ala Ser Ala Tyr Tyr
            115                 120                 125

Pro Ser Ser Phe Pro Lys Lys Lys Tyr Val Asp Gln Ser Asp Arg Ala
        130                 135                 140

Gly Gly Pro Arg Ala Phe Ser Glu Val Pro Asp Arg Ala Pro Asp Ser
145                 150                 155                 160

Arg Pro Glu Glu Ala Leu Asp Ser Ser Arg Gln Leu Gln Ala Asp Ile
                165                 170                 175

Leu Ala Ala Thr Gln Asn Leu Lys Ser Pro Thr Arg Ala Ala Leu Gly
                180                 185                 190

Gly Gly Asp Gly Ala Arg Met Val Glu Gly Arg Gly Ala Glu Glu Glu
            195                 200                 205

Glu Lys Gly Ser Gln Glu Gly Asp Gln Glu Val Gln Gly His Gly Val
        210                 215                 220

Pro Val Glu Thr Pro Glu Ala Gln Glu Glu Pro Cys Ser Gly Val Leu
225                 230                 235                 240

Glu Gly Ala Val Val Ala Gly Glu Gly Gln Glu Leu Glu Gly Ser
                245                 250                 255

Leu Leu Leu Ala Gln Glu Ala Gln Gly Pro Val Gly Pro Pro Glu Ser
            260                 265                 270
```

-continued

```
Pro Cys Ala Cys Ser Ser Val His Pro Ser Val
        275                 280

<210> SEQ ID NO 2
<211> LENGTH: 14
<212> TYPE: PRT
<213> ORGANISM: Homo sapiens

<400> SEQUENCE: 2

Val Ala Gly Ser Gly Glu Ala Glu Gly Ser Ser Ala Ser Ser
1               5                   10

<210> SEQ ID NO 3
<211> LENGTH: 16
<212> TYPE: PRT
<213> ORGANISM: Homo sapiens

<400> SEQUENCE: 3

Met Gly Pro Gln Pro Ile Thr Leu Gly Gly Pro Ser Pro Pro Thr Asn
1               5                   10                  15
```